(12) United States Patent
Onuki et al.

(10) Patent No.: US 8,206,407 B2
(45) Date of Patent: Jun. 26, 2012

(54) MEDICAL PROCEDURE TOOL

(75) Inventors: Yoshio Onuki, Tokyo (JP); Satoshi Miyamoto, Tokyo (JP)

(73) Assignee: Olympus Corporation (JP)

( * ) Notice: Subject to any disclaimer, the term of this patent is extended or adjusted under 35 U.S.C. 154(b) by 691 days.

(21) Appl. No.: 11/399,664

(22) Filed: Apr. 6, 2006

(65) Prior Publication Data
US 2006/0259044 A1   Nov. 16, 2006

Related U.S. Application Data

(63) Continuation of application No. PCT/JP2004/015000, filed on Oct. 5, 2004.

(30) Foreign Application Priority Data

Oct. 8, 2003   (JP) ................ P2003-349571

(51) Int. Cl.
*A61B 17/10*   (2006.01)
(52) U.S. Cl. ...................................... 606/139
(58) Field of Classification Search .......... 606/139, 606/144–150, 138, 171
See application file for complete search history.

(56) References Cited

U.S. PATENT DOCUMENTS

| | | | |
|---|---|---|---|
| 5,176,691 A | 1/1993 | Pierce | |
| 5,242,459 A | 9/1993 | Buelna | |
| 6,554,845 B1* | 4/2003 | Fleenor et al. | 606/148 |
| 2003/0144673 A1* | 7/2003 | Onuki et al. | 606/139 |
| 2003/0181926 A1* | 9/2003 | Dana et al. | 606/148 |

FOREIGN PATENT DOCUMENTS

| | | |
|---|---|---|
| JP | S48-71090 | 9/1973 |
| JP | S54-30692 | 3/1979 |
| JP | 11-511362 | 10/1999 |
| JP | 2001-440 | 1/2001 |
| JP | 2003-19139 | 1/2003 |
| JP | 2003-204966 | 7/2003 |
| WO | WO 97/09935 | 3/1997 |

OTHER PUBLICATIONS

International Search Report PCT/JP2004/015000 dated Dec. 2, 2004.
Notice of Allowance mailed Jul. 14, 2009 in corresponding Japanese Patent Application No. 2003-349571 (with English language translation).

* cited by examiner

*Primary Examiner* — Gary Jackson
*Assistant Examiner* — Erin Colello

(57) ABSTRACT

A medical procedure tool equipped with:
a flexible linear material for carrying out a specific procedure to a biological tissue;
a linear material holding member provided covering the linear material in a freely advancing and retracting manner, for holding the linear material;
a flexible first sheath provided so as to come into contact with the base end side of the linear material holding member;
a flexible second sheath provided so as to be freely advancing and retracting with respect to the first sheath and the linear material holding member;
an operator for advancing and retracting manipulation of the second sheath; and
a cutting means for cutting the linear material; wherein
the cutting means is provided with a first cutting part provided to the linear material holding member; and a second cutting part that is provided to the front end of the second sheath and which, together with the first cutting part, grips the linear material there between; and
one of either the first cutting part or the second cutting part is a blade member.

4 Claims, 14 Drawing Sheets

MEDICAL PROCEDURE TOOL

CROSS REFERENCE TO RELATED APPLICATION

The is a continuation application of PCT/JP2004/015000 filed Oct. 5, 2004, which claim priority to Japanese Patent Application 2003-349571 filed Oct. 8, 2003, which is hereby incorporated by reference. The PCT International Application was published in the Japanese language.

TECHNICAL FIELD

The present invention relates to a medical procedure tool which is inserted into a body cavity and employed to carry out a specific procedure, such as ligation or suturing of a biological tissue.

BACKGROUND ART

A variety of medical procedure tools have been proposed that are introduced into a body cavity by insertion through the instrument channel of an endoscope and used to carry out specific procedures such as ligation, suturing, or sampling of biological tissues. One example of this type of medical procedure tool is a conventionally known medical ligation unit such as disclosed in Japanese Unexamined Patent Application, First Publication No. 2003-204966 (paragraphs 0020-0040, FIGS. 1 to 5). This medical ligation unit enables the process of ligating a lesion site inside a body cavity using a ligating wire, and cutting the tightened ligating wire to be carried out as a series of operations.

This medical ligation unit is equipped with a medical ligation tool which is retained inside the body, and an operating device for guiding the medical ligation tool into the body and then performing the ligating operation. The medical ligation tool is provided with the aforementioned ligating wire, which has a folded over portion at its base end side, and a receiving member, which is for holding the ligating wire at the front of the folded over portion in a manner to permit free advance and retraction. The receiving member has an annular projection located at roughly the center along its axial direction, and is for exposing the ligating wire to the outside, while at the same time serving as the contact surface for the cutting blade, explained below.

The operating device has an inner sheath that comes into contact with the base end side of the receiving member. A finger ring is connected to the base end side of the inner sheath via the main body of the operator. The receiving member engages with the front end of the inner sheath. A slider that is freely advancing and retracting with respect to the operator main body is attached to the operator main body. An operating wire, which is inserted through the inner sheath and has an engaging member at its front end, is connected to this slider. This engaging member is designed to engage with the folded over portion of the ligating wire. In other words, by fixing the operator main body in place and then advancing or retracting the slider, the diameter of the ligating wire can be increased or decreased.

A cutting sheath is provided to the periphery of the inner sheath, and covers this inner sheath in a freely advancing and retracting manner. A cutting operator is connected to the base end side of the cutting sheath. This cutting operator is disposed to the front end side of the operator main body, and comes into contact with the operator main body so that it cannot move in the base end direction. An annular cutting blade is formed at the front end of the cutting sheath.

When ligating a lesion site inside a body cavity using a medical ligation unit designed as described above, the medical ligation unit is first attached to the procedure device. Namely, the receiving member is supported by the inner sheath as a result of catching the folded over portion of the ligating wire on the engaging member of the operating wire, engaging the receiving member in the front end of the inner sheath, and then the moving the slider in the base end direction. This arrangement unit is then introduced into the body cavity via an endoscope device or the like, and the ligating wire is then slipped around the lesion site. In this arrangement, the operator main body is fixed in place, the slider is moved toward the base end direction, and the diameter of the ligating wire is reduced. As a result, the lesion site is tied off, cutting off blood flow to the site. Once tied off, with the operator main body fixed in place, the cutting operator is pushed in the forward direction. Namely, the cutting sheath is moved in the forward direction along the inner sheath.

As a result, the cutting blade formed at the front end of the cutting sheath is moved toward the annular projection on the receiving member, and the ligating wire that is externally exposed at this annular projection is cut. After cutting the ligating wire, the cutting blade comes into contact with the contact surface of the annular projection. As a result, the ligating wired tying off the lesion site is cut away and the ligating procedure is completed. When the ligating wire is cut, the receiving member falls out from the inner sheath and drops into the body, where it is subsequently naturally eliminated.

The present invention was conceived in view of the above-described circumstances, and has as its objective the provision of a medical procedure tool for cutting a linear material such as ligating wire or the like with certainty after performing a specific procedure to a biological tissue, while at the same time not requiring overly troublesome procedures following cutting.

DISCLOSURE OF THE INVENTION

The present invention provides the following means in order to achieve the above-described objectives.

The first aspect of the present invention provides a medical procedure including:

a flexible linear material for carrying out a specific procedure to a biological tissue;

a linear material holding member provided covering the linear material in a freely advancing and retracting manner, for holding the linear material;

a flexible first sheath provided so as to come into contact with the base end side of the linear material holding member;

a flexible second sheath provided covering the first sheath and so as to be freely advancing and retracting with respect to the first sheath and the linear material holding member;

an operator that is connected to the base end side of the second sheath and is for advancing and retracting manipulation of the second sheath; and a cutting means for cutting the linear material; wherein
the cutting means is provided with a first cutting part provided to the linear material holding member; and a second cutting part that is provided to the front end of the second sheath disposed farther forward than the first cutting part and which, together with the first cutting part, grips the linear material therebetween; and
one of either the first cutting part or the second cutting part is a blade member.

In the medical procedure tool according to the first aspect of the present invention, once a specific procedure has been performed to the biological tissue using the linear material, the device is manipulated to pull the operator toward the base end direction, and the second sheath is retracted with respect to the first sheath. As a result, the second cutting part moves toward the first cutting part that is provided to the linear material holding member. The linear material is then cut in a scissor-like manner by the blade member as it is being held in between the first cutting part and the second cutting part.

Since cutting of the linear material is performed using a pulling manipulation of the second sheath in this manner, the first sheath does not fly out and become exposed from within the second sheath. Accordingly, it is possible to eliminate such troublesome post-cutting procedures as returning the first sheath back inside the second sheath, as is encountered in the prior art. Moreover, since cutting is performed while the linear material is being held in between the two cutting parts, it is possible to cut the linear material easily and with certainty.

The second aspect of the present invention provides the medical procedure tool according to the first aspect of the present invention, wherein the first cutting part has a front end guide for guiding the linear material from inside the linear material holding member to the outside, and a base end guide for guiding the linear material that was guided to the outside by the front end guide back inside; and the second cutting part is disposed to the position where the linear material exposed to the outside is held between the front end guide and the base end guide part.

In the medical procedure tool according to the second aspect of the present invention, the second cutting part moves as a result of the pulling manipulation of the second sheath, and cutting is carried out on the outside of the linear material holding member, as the linear material is being held between the front end guide and the rear end guide.

The third aspect of the present invention provides a medical procedure tool according to the second aspect of the present invention, wherein an opening is on the front end side of the front end of the second sheath, and a slit through which the linear material can be inserted is formed connected to the second cutting part.

When positioning the second cutting part farther forward than the first cutting part in the medical procedure tool according to the third aspect of the present invention, it is possible to position the linear material at the second cutting part via the slit. In other words, by inserting the linear material via the slit so that it may be introduced or withdrawn, it is possible to release and attach the second sheath and the linear material holding member which is holding the linear material. Accordingly, it is possible to exchange only the linear material holding member each time the linear material is cut.

The fourth aspect of the present invention provides the medical procedure tool according to the second aspect of the present invention, wherein the second cutting part is provided to a cutting member that freely attaches to and releases from the second sheath.

Since the cutting member is freely attaching and releasing in the medical procedure tool according to the fourth aspect of the present invention, it is possible to exchange not only the linear material holding member, but also the cutting member, each time cutting is performed. Accordingly, cutting ability does not deteriorate, so that it is possible to maintain the cutting characteristics.

The fifth aspect of the present invention provides a medical procedure tool according to the first aspect of the present invention, wherein the first sheath is a coil sheath.

In the medical procedure tool according to the fifth aspect of the present invention, when the operator is pulled in the direction of the base end, the pulling force acts on the second sheath while a compression force acts on the first sheath. However, since the first sheath is a coil sheath having compressing strength, buckling does not readily occur.

Accordingly, the linear holding member can be held with surety, so that the cutting ability of the linear member can be improved.

The sixth aspect of the present invention provides a medical procedure tool according to the first aspect of the present invention, wherein a reinforcing wire connected to the second cutting part and the operator is fixed in place to the second sheath, along the axial direction thereof.

When manipulating the operator to pull it in the base end direction in the medical procedure tool, the reinforcing wire is fixed in place to the second sheath. As a result, it is difficult to extend in the axial direction, so that the pulling force is communicated with surety to the second cutting part. Accordingly, it is possible to improve the ability to cut the linear material.

The seventh aspect of the present invention provides a medical procedure tool according to the first aspect of the present invention, wherein the linear material is a ligating wire for ligating biological tissue.

After ligating the biological tissue inside the body with this medical procedure tool according to the seventh aspect of the present invention, it is possible cut the ligating wire easily and with certainty. In addition, there is no need for such troublesome procedures as returning the first sheath after cutting, so that the ligating procedure can be carried out with good efficiency.

The eighth aspect of the present invention provides a medical procedure tool according to the first aspect of the present invention, wherein the linear material is a suture material for suturing biological tissue, provided with a pull-out preventing member that is connected to the front end of the suture material, and a suture needle main body for housing the pull-out preventing member and that has a needle part at the front end thereof for penetrating the biological tissue.

BEST MODE FOR CARRYING OUT THE INVENTION

Figure 1:
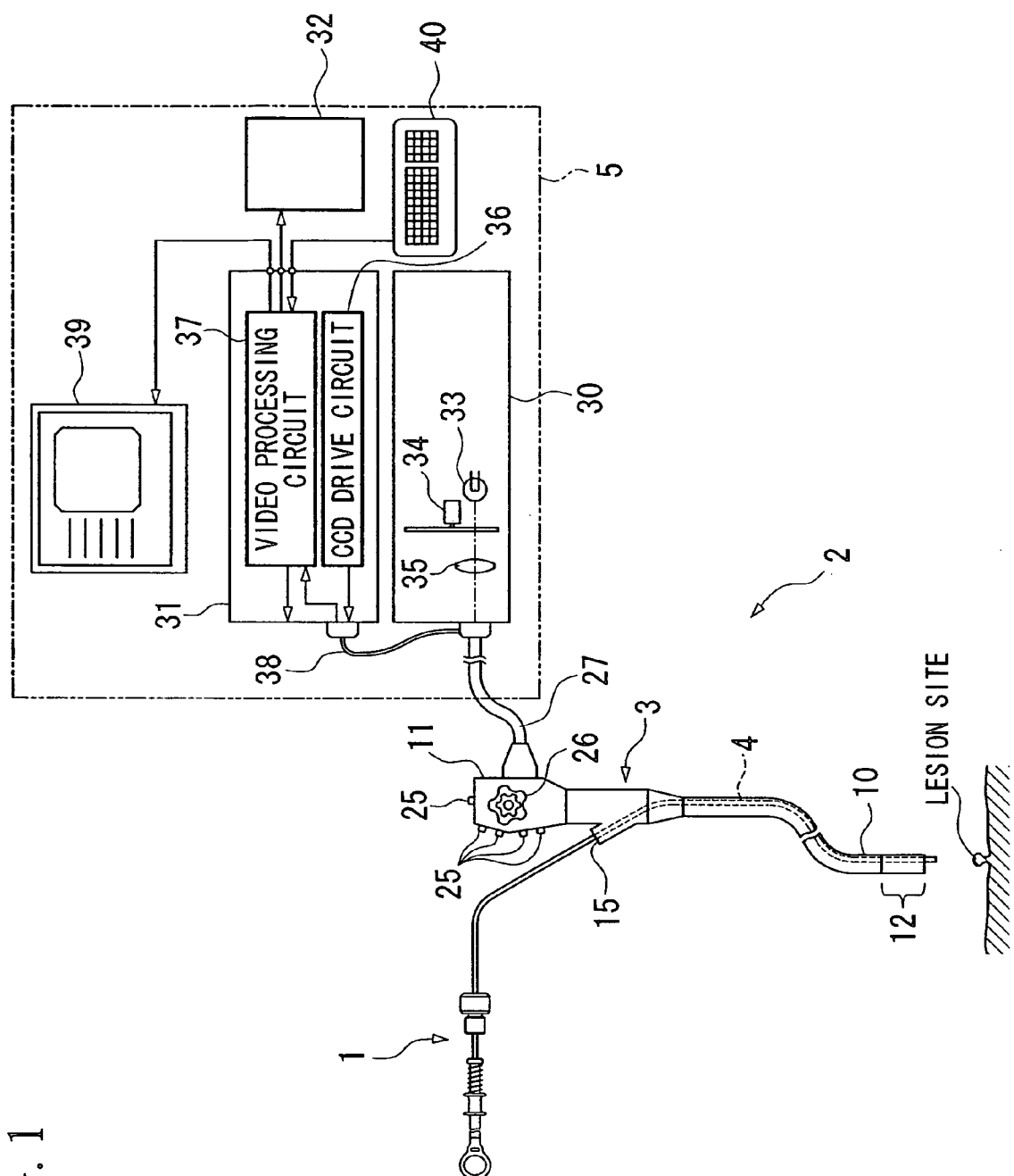
FIG. 1 is a structural view of an endoscope system, provided for explaining a first embodiment of the medical procedure tool according to the present invention.

The first embodiment of the present invention will now be explained with reference to FIGS. 1 through 8. Note, however, that the present invention is not limited thereto. For example, the compositional elements of these various embodiments may be suitably combined.

The medical procedure tool 1 of this embodiment is inserted through the instrument channel 4 of an endoscope device 3, which is a structural component of the endoscope system 2, and is employed to carry out a specific procedure to a biological tissue inside the body. Note that in this embodiment, medical procedure tool 1 is explained as a ligation device for ligating biological tissues. The endoscope system 2 is provided with a endoscope unit 5 for displaying and recording the image picked up by the endoscope device 3.

Figure 2:
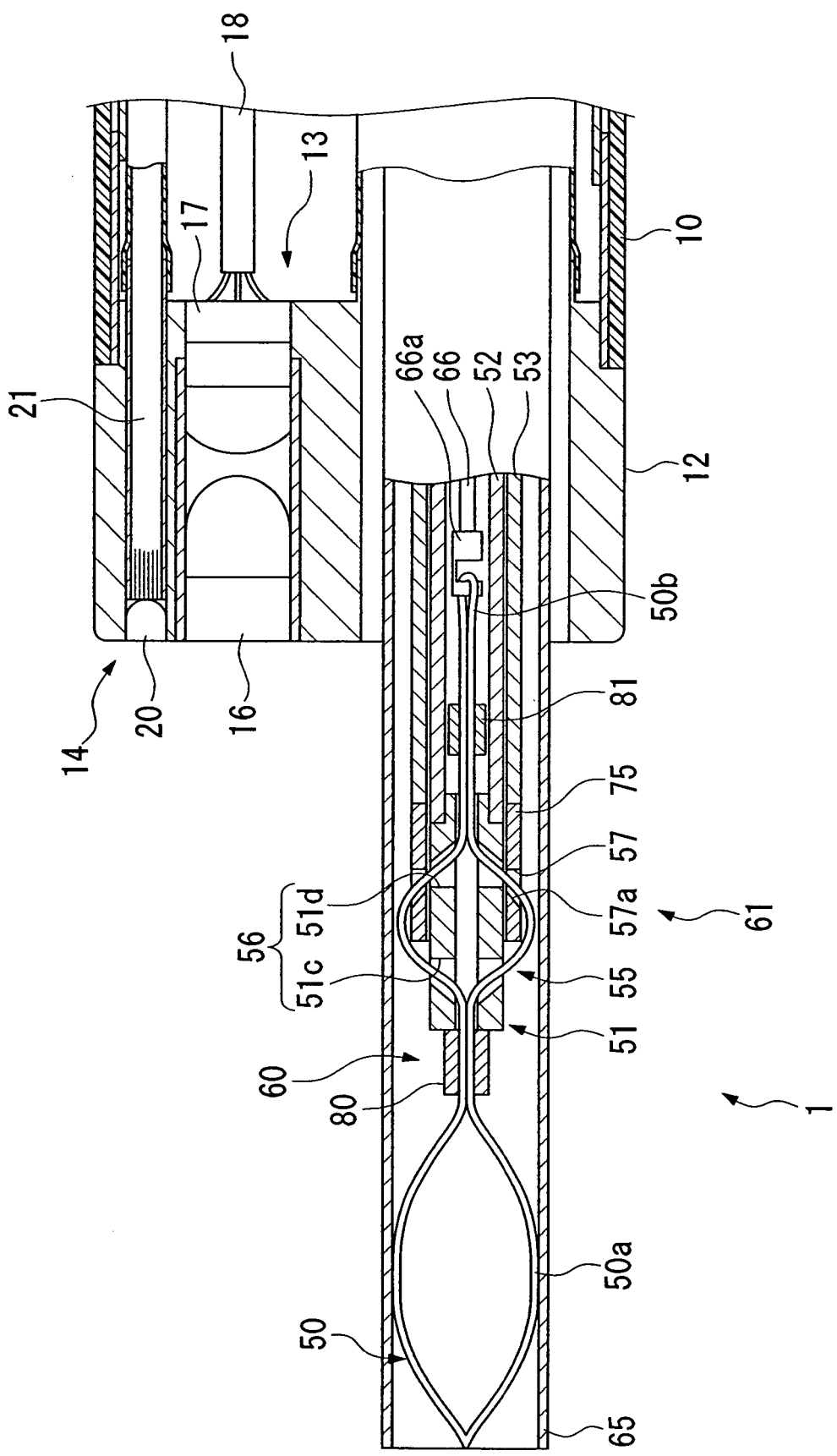
FIG. 2 is a cross-sectional view of the front end of the inserted part of the endoscope, in the endoscope device shown in FIG. 1, showing an arrangement in which the medical procedure tool has been inserted into an instrument channel.

As shown in FIGS. 1 and 2, the endoscope device 3 is provided with a long flexibly bending inserted part 10 which is inserted into the body, and an operator 11 that is connected to the base end of the endoscope inserted part 10. A bending part 12, the angle for which can be freely and optionally set, is connected at the front end of the inserted part 10, and a view pick-up unit 13 for viewing the inside of the body, and an illuminating member 14 for radiating illuminating light supplied from the endoscope unit 5 inside the body are provided to the front end of the bending part 12. An instrument channel 4 is formed extending along the longitudinal direction within the endoscope inserted part 10, from the instrument insertion port 15 provided near the operator 11 to the front end of the endoscope inserted part 10.

As shown in FIG. 2, the view pick-up unit 13 consists of an optical system 16 for viewing use, such as an objective lens, that is disposed to the front end of the inserted part 10, i.e., to the front end of the bending part 12, of the endoscope, and an endoscope CCD 17, which is an individual image pick-up element that is disposed to the image forming position on the viewing-use optical system 16. A cable 18 connected to the endoscope CCD 17 passes through the inside of the inserted part 10 of the endoscope, is pulled out to the rear of the endoscope CCD 17 and is connected to the endoscope unit 5.

The illuminating member 14 has an illuminating lens 20 disposed to the front end of the endoscope inserted part 10, i.e., the front end of the bending part 12, and a LG fiber bundle 21, which is a bundle of optical fibers for guiding illuminating light supplied from the endoscope unit 5 to the illuminating lens 20.

As shown in FIG. 1, the operator 11 is provided with a plurality of switches 25 and an operating knob 26. These switches 25 are programmable switches in which specific functions can be set. For example, one of these is designed to function as a switch which is depressed when recording the endoscope image that is being picked up by the endoscope CCD 17. The device is designed so that the signal of these switches 25 is relayed to an endoscope unit 5 via a cable 27.

The operating knob 26 is designed to bend the bending part 12 in an optional direction, thereby controlling the direction of inclination of the objective lens 16, illuminating lens 14 and exit port of the instrument channel 4 that are disposed to the front end of the bending part 12. As a result, it is possible to view the inside of the body from an optional angle.

The endoscope unit 5 has a light source device 30 for supplying illuminating light onto the illuminating lens 20; a processor 31 which is connected to the rear of the cable 18, which in turn is connected to the endoscope CCD 17 and is for processing the image signal captured by the endoscope CCD 17; and a recording device 32 which is connected to the processor 31 and is for recording the image signal output from the processor 31.

The light source device 30 is provided with a lamp 33 for generating white light; a rotation filter 34 to which is attached a red, blue and green color transmitting filter for converting the white light generated from the lamp 33 to a frame sequential method; and a converging lens 35 for converging the frame sequential light and incidenting it on the LG fiber bundle 21. The operation of the lamp 33 is controlled by one of the switches 25 that is disposed to operator 11.

The processor 31 is provided with a CCD drive circuit 36 for driving the endoscope CCD 17, and a video processing circuit 37 for performing signal processing of the captured image signal output from the endoscope CCD 17 and generating a video signal. The processor 31 is connected to a cable 27 via a cable 38, and is designed so that the CCD drive signal from the CCD drive circuit 36 is relayed to the endoscope CCD 17, while at the same time the captured image signal from the endoscope CCD 17 is sent to the video processing circuit 37. The processor 31 is designed so that the video signal is output to a recording device 32 such as a hard disk, and a monitor 39 such as a display, based on the signals from the switches 25 which are relayed via the cables 38, 27. Further, an input means 40 such as a keyboard or the like is connected to the processor 31, and various information such as the test subject's name, ID number, diagnostic information and the like can be added to the video picked up by the endoscope CCD 17.

Figure 3:
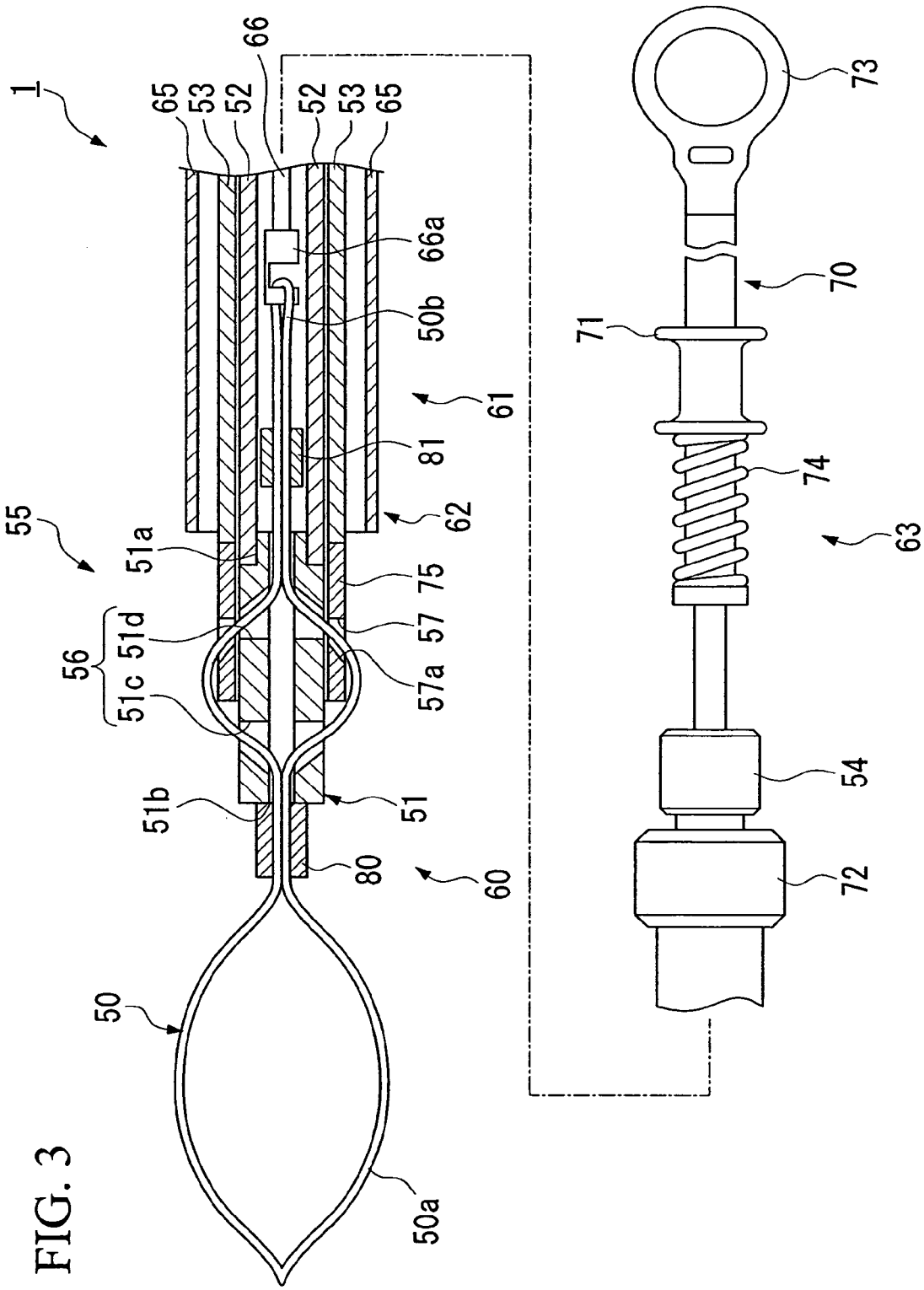
FIG. 3 is a structural view showing the medical procedure tool of the embodiment shown in FIG. 1.

As shown in FIG. 3, the above-described medical procedure tool 1 is equipped with a flexible ligating wire (linear material) 50 for carrying out a specific procedure, such as ligation, to a biological tissue; a wire holding member (linear material holding member) 51 which is provided covering the ligating wire 50 in a freely advancing and retracting manner, for holding the ligating wire 50; a flexible inner sheath (first sheath) 52 which is provided in contact with the base end side of the wire holding member 51; a flexible cutting sheath (second sheath) 53 provided covering the inner sheath 52, in a freely advancing and retracting manner with respect to the inner sheath 52 and the wire holding member 51; a cutting operator (operator) 54 which is connected to the base end side of the cutting sheath 53 and is for advancing and retracting manipulation of the cutting sheath 52; and a cutting means 55 which is for cutting the ligating wire 50.

The cutting means 55 has a first cutting part 56 which is provided to the wire holding member 51; and a side hole (second cutting part) 57 which is provided to the front end of the inner sheath 52, disposed farther forward than the first cutting part 56, for gripping, together with the first cutting part 56, the ligating wire 50 therebetween. At least one of the first cutting part 56 and the side hole 57 forms a blade member, which will be explained in further detail below.

The medical procedure tool 1 according to this embodiment is composed of a medical ligation tool 60 which is retained inside the body, and an operating device 61 for guiding the medical ligation tool 60 inside the body and carrying out the ligating operation. Operating device 61 is composed of a flexible inserted part 62 which is inserted into the instrument channel 4, and a hand operator 63.

The inserted part 62 is composed of an outer sheath 65 which formed of a flexible plastic such as polyethylene, PTFE or the like; a cutting sheath 53 which is inserted in a freely advancing and retracting manner into the outer sheath 65; an inner sheath 52 which is disposed inside the cutting sheath 53; and an operating wire 66 which is inserted in a freely advancing and retracting manner into the inner sheath 52 and is formed of a metallic stranded wire such as stainless.

As in the case of the outer sheath 65, the inner sheath 52 and the cutting sheath 53 can be formed of a flexible plastic such as polyethylene, PTFE or the like, for example. A metallic mesh may also be incorporated. In this embodiment, a metallic coil sheath is employed for the inner sheath 52 and the cutting sheath 53.

The hand-held operator 63 is composed of an operator main body 70 connected to the base end side of the inner sheath 52; a slider 71 which is connected to the base end side of the operating wire 66, and covers the operator main body 70 in a freely advancing and retracting manner with respect thereto; a cutting grip 54; and a grip 72 that is connected to the base end side of the outer sheath and is for advancing and retracting manipulation of the outer sheath 65.

A finger ring 73 is formed to the base end side of the operator main body 70. In addition, the slider 71 is provided with a shape such that the center area thereof is indented with respect to either of the edge portions of the slider. As a result, by placing the thumb in the finger ring 73, and holding the slider 71 between the index and middle fingers, the slider 71 can be advanced and retracted with one hand. The slider 71 is connected to a spring 74, which is connected to the front end of the operator main body 70, so that the slider 71 remains at roughly the center position of the operator main body 70. In other words, the slider 71 is designed so that it will return to its original position following manipulation in the direction of the finger ring 73 (i.e., the base direction), once the finger is released.

A cutting grip 54 is disposed farther toward the front end than the operator main body 70. When this cutting grip 54 is moved in the base end direction, it comes into contact with the front end of the operator main body 70 and cannot move farther toward the base end.

By advancing and retracting this grip 72, cutting grip 54, and slider 71, the outer sheath 65, the cutting sheath 53, the inner sheath 52 and the operating wire 66 can be manipulated relative to one another.

Figure 4:
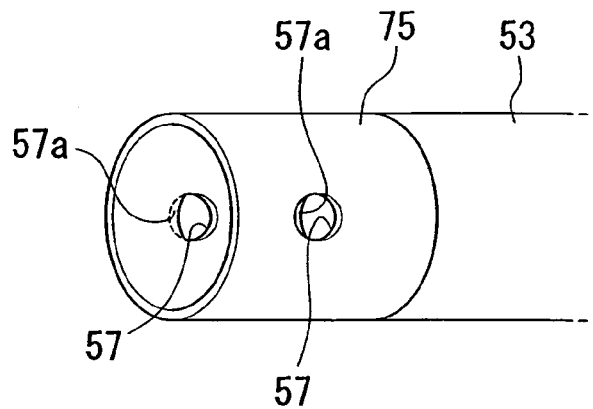
FIG. 4 is a perspective view showing the medical ligation tool in the medical procedure tool shown in FIG. 3.

A hook-shaped engaging member 66a is attached in place to the front end of the operating wire 66. As shown in FIG. 4, a cutting member 75 consisting of a metallic member such as stainless, is connected to the front end of the cutting sheath 53 and is formed to have outer and inner diameters that are equal to those of the cutting sheath 53. This cutting member 75 has a pair of side holes 57 which are formed to either side of the cutting member 75 so as to face one another. In this embodiment, the side holes 57 form a blade member. In other words, an acute angle cutting blade 57a for cutting the ligating wire 50 is formed to the front edge of these side holes 57.

Figure 5:
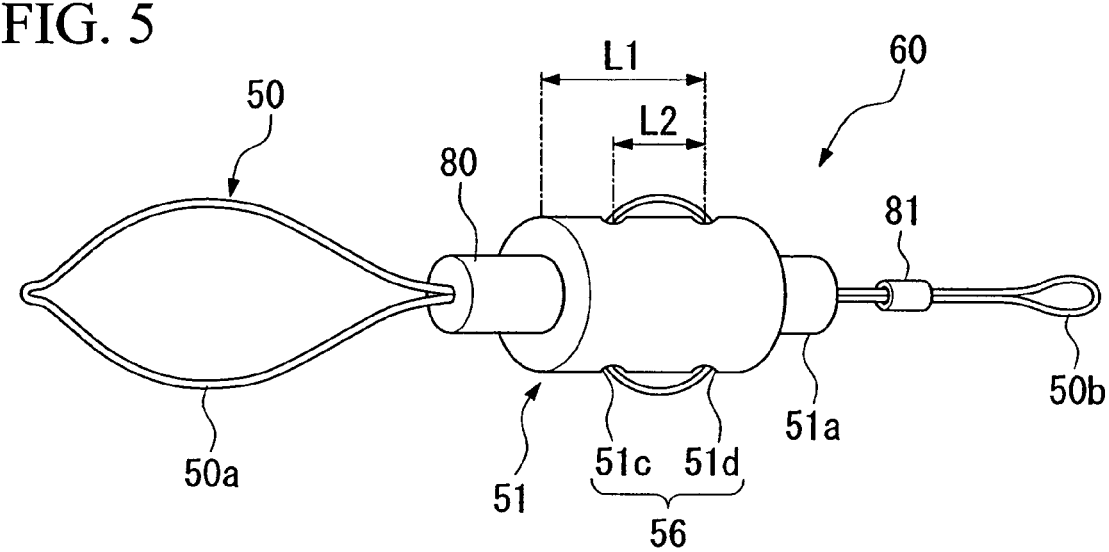
FIG. 5 is a perspective view showing the front end of the cutting sheath in the medical procedure tool shown in FIG. 3.
Figure 6:
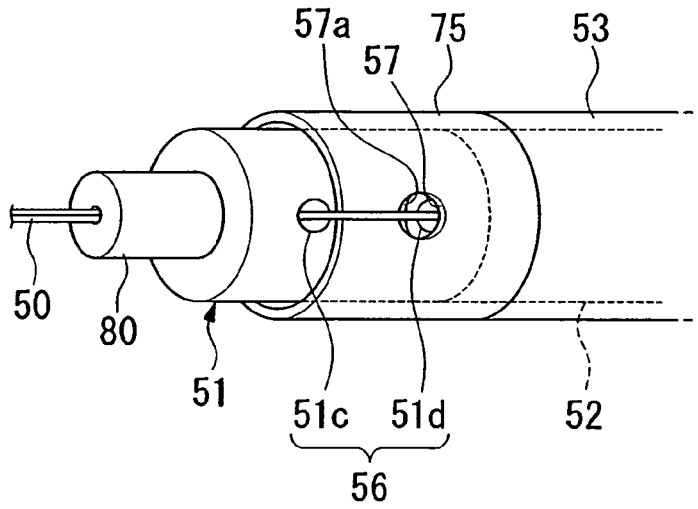
FIG. 6 is a perspective view showing an arrangement in which the medical ligation tool shown in FIG. 5 has been attached to the front end of the cutting sheath shown in FIG. 4.

As shown in FIGS. 3 and 5, the medical ligation tool 60 is provided with a ligating wire 50, a wire holding member 51, and a stopper 80 which is provided near the front end of the wire holding member 51.

The ligating wire 50 is formed from a synthetic resin such as nylon or polyolefin, silk, or an absorbable filament, and is provided with a loop portion 50a farther toward the front end side than the stopper 80. The ligating wire 50 may be in the form of a monofilament, stranded fiber or metal filament. A folded over portion 50b that can engage with the engaging member 66a is formed to the base end side of the ligating wire 50. Either end and the two parallel strands of the ligating wire 50 are fixed in place with an adhesive or pressure by a connecting pipe 81 which is employed as a fixing tool.

Stopper 80 is a fixing member for fixing the ligating wire 50 in place at an optional position, and consists of a rubber such as silicon or fluorinated rubber, various types of thermoplastic elastomers, or a knot in the filament. This stopper 80 is in the form of a freely advancing and retracting tubular body that covers the ligating wire 50. Namely, the diameter of the loop part 50a can be decreased by moving the stopper 80 toward the front end, or can be increased by moving the stopper 80 toward the base end.

The wire holding member 51 is formed in a cylindrical shape from a metal member such as stainless, or a plastic such as polypropylene, ABS, polyacetal, polycarbonate or the like. A reduced diameter part 51a having a small outer form is formed on the base end side of the wire holding member 51. This reduced diameter part 51a is designed to be insertable into the front end of the inner sheath 52, and to be supported in the inner sheath 52 once inserted. In this case, a step is generated between the outer peripheral surface of the inner sheath 52 and the outer peripheral surface of the wire holding member 51. As a result, the cutting sheath 53 is designed so as to advance and retract smoothly with respect to the inner sheath 52 and the wire holding member 51.

A front end hole 51b is formed in the middle of the front end surface of the wire holding member 51. This front end hole 51b is for passing the ligating wire 50, which has been passed through the stopper 80, into the wire holding member 51. In addition, a pair of front end side holes (front end guides) 51c and a pair of base end side holes (base end guides) 51d are formed at the approximate center area of the wire holding member 51. The front end side holes 51c are for guiding the ligating wire 50 which has been introduced into the wire holding member 51 via the front end holes 51b, to the outside of the wire holding member 51. The base end side holes 51d are for guiding the ligating wire 50 which has been drawn to the outside of the wire holding member 51 via the front end side holes 51c, back inside the wire holding member 51. These front end side holes 51c and base end side holes 51d form the first cutting part 56.

In the present embodiment, the medical ligating tool 60 and the operating device 61 are assembled in advance as a unitary structure, and the ligating wire 50 is designed to pass through front end side holes 51c, then through side holes 57 and then be inserted into the base end side holes 51d. In other words, the ligating wire 50 is assembled as described above, while at the same time, the reduced diameter part 51a of the wire holding member 51 is introduced into the front end of the inner sheath 52 and engages there, to form a unitary assembly.

The inside surface of the front end side of the front end side holes 51c and the inside surface of the back end side of the base end side holes 51d are designed to form an inclined surface. As a result, this facilitates feeding of the ligating wire 50 from the inside of the wire holding member 51 to the outside, and from the outside of the wire holding member 51 to the inside, and, also makes it easier to pull out the ligating wire 50. The front end side holes 51c and the base end side holes 51d are formed so as to be positioned on the same axis as the wire holding member 51.

In the addition, as shown in FIG. 5, in the present embodiment, the distance L1 between the front end surface of the wire holding member 51 and the base end side holes 51d is 5 mm, for example, while the distance L2 between the front end side holes 51c and the base end side holes 51d is 2~3 mm, for example. However, since these distances L1 and L2 correlate to the length of the ligating wire 50 that remains after cutting by the cutting blade 57a of the side holes 57, which will be explained below, it is desirable to set these lengths to be as short as possible.

Ligation of a lesion site in a biological tissue inside the body using a medical procedure tool 1 designed as above will now be explained.

The desired switch 25 which is disposed to the operator 11 shown in FIG. 1 is depressed, to cause operation of the light source device 30. As a result, illuminating light generated from the light source device 30 is emitted from the illuminating lens 14 via the LG fiber bundle 21. The CCD drive circuit 36 inside the processor 31 is operated to drive the endoscope CCD 17.

In this state, the endoscope inserted part 10 is introduced into the test subject's body via the mouth, for example. In this case, by operating the operating knob 26 which is provided to the operator 11, the bending part 12 on the front end of the endoscope inserted part 10 is inserted while at the same being inclined in the desired direction. As a result, the endoscope inserted part 10 can be smoothly inserted into the body and the radiation of illuminating light on the site desired to be viewed can be carried out with assurance.

The captured image signal which is picked up by the endoscope CCD 17 via the objective lens 16 is relayed to the processor 31 via the cables 18, 27, and 38, and is converted to a video signal by the video processing circuit 37. The converted video signal is recorded by the recording device 32, relayed to a monitor 39 and displayed as the endoscope image. In this case, by inputting specific information such as the test subject's name, ID number, the area being visualized, etc., via the input means 40, this information can be displayed along with the endoscope image on the monitor 39.

After confirming via the endoscope image shown on the monitor 39 that the front end of the endoscope inserted part 10 has reached the lesion site where the ligation is to be performed, the medical specialist positions the front end of the inserted part 10 of the endoscope near the lesion site while watching the monitor 39. Next, in this state, the medical specialist inserts the medical procedure tool 1 into the instrument channel 4 via the instrument insertion port 15 of the endoscope device 3. In this case, the grip 72 is moved in the forward direction, and, with the loop portion 50a of the ligating wire 50 covered by the outer sheath 65, the outer sheath 65 is inserted into the instrument channel 4.

In other words, the loop portion 50a is housed in a closed state within the outer sheath 65. In this case, the slider 71 is positioned at roughly the center of the operator main body 70 by the spring 74, and movement in the forward direction is restricted. Namely, the operating wire 66 cannot readily move in the forward direction. Accordingly, the device is designed so that the engaging member 66a does not fly out unintentionally from the front end of the inner sheath 52, and the inner sheath 52 and the wire holding member 51 do not become loose, when the operating wire 66 is inserted into the instrument channel 4.

Further, after confirming that the inserted part 62 is projecting out from the front end surface of the endoscope inserted part 10 based on the endoscope image displayed on the monitor 39, the medical specialist moves the grip 72 in the direction of the base and retracts the outer sheath 65 until the cutting member 75 is exposed. As a result, as shown in FIG. 3, the loop part 50a of the ligating wire 50 is released from within the outer sheath 65 and is elastically restored so that its diameter expands. Once the diameter of the loop part 50a has been expanded, the medical specialist manipulates the endoscope to draw the loop part 50a around the lesion site, while concurrently visually confirming the endoscope image displayed on the monitor 39.

After suspending the loop part 50a around the lesion site, the slider 71 is moved in the direction of the base end and the operating wire 66 is retracted. As a result, the ligating wire 50 is moved in the direction of the base end via the engaging member 66a. In this case, the stopper 80 moves in the forward direction relatively, so that the diameter of the loop portion 50 is reduced and the lesion site is tied off (ligated). Blood flow to the lesion site is cut off as a result of this ligation. When operating the slider 71, the medical specialist can carry out operations easily with one hand while watching the monitor 39, by employing the finger ring 73 as described above. Ligation of the lesion site can be easily carried out when once the loop portion 50a has been drawn around the lesion site, by positioning the stopper 80 so as to press against the lesion site.

Figure 7:
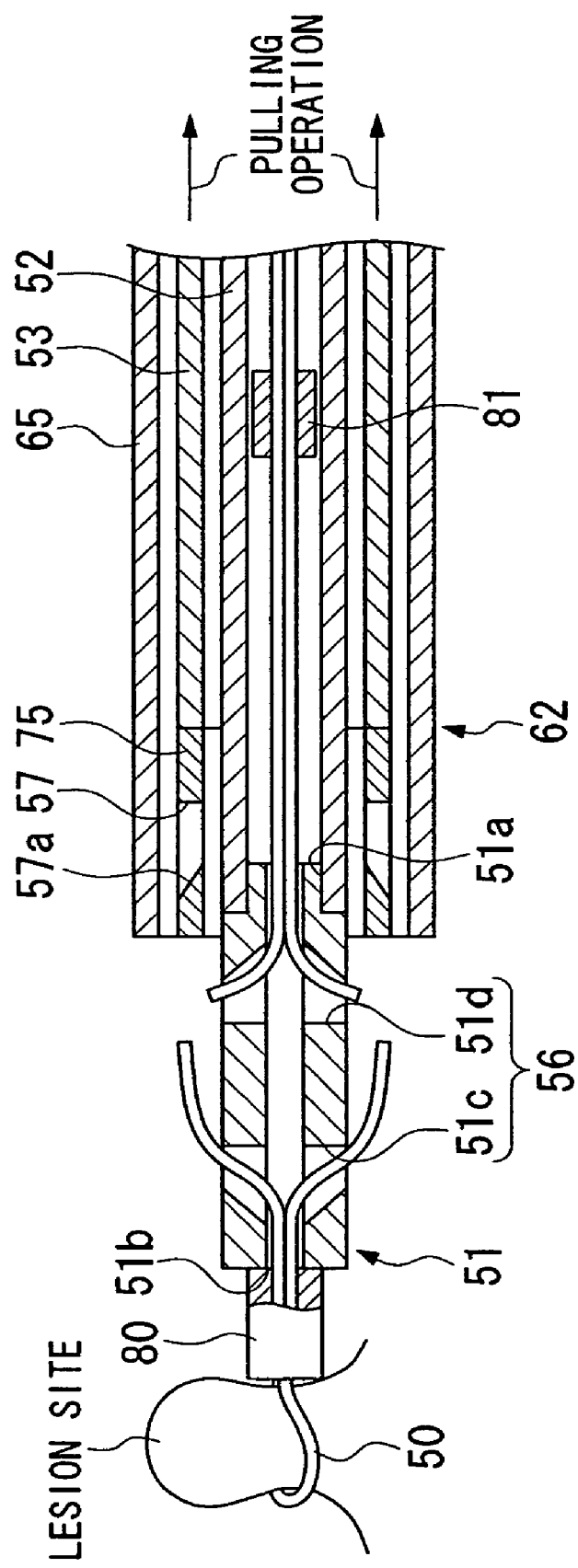
FIG. 7 is a cross-sectional view showing the arrangement in which a lesion site has been ligated using the medical procedure tool shown in FIG. 3, followed by cutting of the ligating wire.

After confirming that the lesion site has been tied off with certainty by using the endoscope image displayed on the monitor 39, the medical specialist moves the cutting grip 54 in the direction of the base end and retracts the cutting sheath 53. When the cutting sheath 53 is retracted, the side holes 57 of the cutting member 75 are moved toward the base end side holes 51*d* of the wire holding member 51. Then, as shown in FIG. 7, scissor-like cutting of the ligating wire 50 is carried out by cutting blade 57*a* as the ligating wire 50 is held between the side holes 57 and the base end side holes 51*d*.

In the medical procedure tool 1 of the present embodiment it is possible to carry out cutting of the ligating wire 50 by pulling the cutting grip 54 in the direction of the base end, and performing a tugging operation. Accordingly, hypothetically, even if the cutting grip 54 were pulled toward the hand-held side by applying force in order to carry out cutting, the inner sheath 52 does not fly out and become exposed from the cutting sheath 53 due to force during cutting. Here, when cutting the ligating wire 50 by pushing in the cutting grip 54, for example, the ligating wire 50 is cut when the cutting grip 54 is pushed in with force, while at the same time there is a possibility that the inner sheath 52 will move in the forward direction as the cutting grip 54 pushes the grip 72 from the rear due to the pushing force. As a result, there is a chance that the inner sheath 52 will fly out from the cutting sheath 53 and become exposed. Accordingly, it is necessary to perform the troublesome procedure of manually reinserting the inner sheath 52 into the cutting sheath 53 each time the ligating wire 50 is cut.

However, in this embodiment, the ligating wire 50 is cut by the tugging operation of the cutting grip 54, so that the inner sheath 52 does not become exposed after cutting and the above-described troublesome procedures following cutting can be eliminated. Accordingly, it is possible to eliminate the time and trouble associated with returning the inner sheath 52 to its original position, so that a more efficient ligation device can be realized.

In particular, when moving the cutting grip 54 in the base end direction, it comes into contact with the front end of the operator main body 70 and cannot move further. As a result, even if force is introduced, it is possible to carry out a safe tugging operation.

Since cutting is performed with the ligating wire 50 held between the side holes 57 and the base end side holes 51*d*, it is possible to cut the ligating wire 50 easily and with certainty.

The inner sheath 52 is a coil sheath having compressive strength, so that buckling and contraction do not readily occur. Accordingly, when performing the tugging operation on the cutting grip 54, the wire holding member 51 can be held with certainty, even if a force which is directed relatively compressively is applied on the inner sheath 52. As a result, cutting ability can be improved.

When cutting the ligating wire 50, it is preferable to support the slider 71 in the state where it is pulled toward the direction of the base. In this way, tension can be applied on the ligating wire 50 via the operating wire 66 and the engaging member 66*a*, so that cutting ability can be improved. Hypothetically, even if a time difference occurs such that the two ligating wires 50 shown in FIG. 7 are not simultaneously cut, the two ligating wires 50 are joined via the connecting pipe 81. As a result, even if one of the ligating wires 50 is cut, tension can still be applied with certainty on the other ligating wire 50, so that the cutting ability is not diminished.

As shown in FIG. 7, the base direction side of the cut ligating wire 50 is pulled in the base direction by the operating wire 66 via the engaging member 66*a*. As a result, the cut ends are passed through the inside of the wire holding member 51, and pulled into the inner sheath 52. In this case, the cut ends of the ligating wire 50 can be smoothly pulled without getting stuck due to the inclined surface of the base end side holes 51*d*.

After confirming that the cutting of the ligating wire 50 has been carried out with certainty by viewing the endscope image shown on the monitor 39, i.e., by viewing the image of the cut ligating wire 50, the medical specialist operates the endoscope to slowly move the front end of the inserted part 62 away from the lesion site. In this case, the cut ends on the front end side of the ligating wire 50 are inserted inside from the front end side holes 51*c* of the wire holding member 51, while at the same time being pulled out to the outside from front end hole 51*b*. In this case, ligating wire 50 is easily pulled out due to the inclined surface of the base end side holes 51*d* and, similarly, the inclined surface of the front end side holes 51*c*, thus, there is no impact on the tying down state at the lesion side, and the operation of separating the inserted part 62 can be carried out easily.

Figure 8:
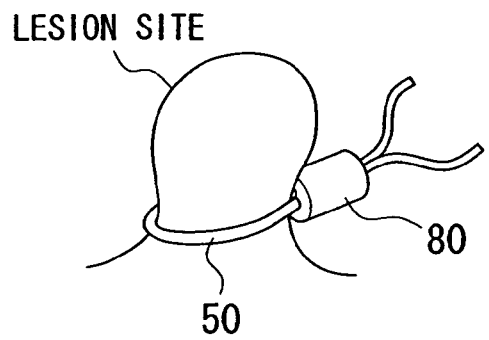
FIG. 8 is a perspective view of the lesion site showing the condition after cutting of the ligating wire.

As a result, as shown in FIG. 8, the procedure for tying off the lesion site is concluded leaving only the ligating wire 50, which is held in the tied down state by stopper 80, retained inside the body.

Stopper 80 fixes the ligating wire 50 in place as a result of the frictional force between its inner peripheral surface and the ligating wire 50, thereby maintaining the tied off state. Hypothetically, even if the wire holding member 51 falls out from the inner sheath 52, i.e., even if the engagement between the reduced diameter part 51*a* and the inner sheath 52 is released, when pulling out a medical procedure tool 1 from the instrument channel 4 after completion of the ligating process, the wire holding member 51 is naturally eliminated from the body via the digestive tract.

In this embodiment, the wire holding member 51 is formed so as to engage with the inner sheath 52 by means of the insertion of the reduced diameter part 51*a* into the front end of the inner sheath 52, and it was disclosed that there is a possibility that the wire holding member 51 could fall off depending on the circumstances after cutting. However, the present embodiment is not limited to this design. For example, a design is also acceptable in which a wire holding member 51 is provided to the front end of the inner sheath 52 in a manner so as to become free from the inner sheath 52 after cutting of the ligating wire 50. Alternatively, a design is also acceptable in which the inner sheath 52 and the wire holding member 51 are assembled in a unitary manner, after which they are engaged with the front end of the inner sheath 52 and fixed in place so that the wire holding member 51 does not come free.

Next, the second embodiment of the medical procedure tool according to the present invention will be explained with reference to FIGS. 9 through 11. Structural elements that are the same as those in the first embodiment will be assigned the same numeric symbol, and an explanation thereof will be omitted.

The point of difference between the first embodiment and the second embodiment is that in the medical procedure tool 1 according to the first embodiment, the second cutting part comprises the side holes 57, which are complete holes provided to the peripheral surface of the cutting member 75. In contrast, in the medical procedure tool 90 according to the second embodiment, a slit 91 is formed to the front end of the cutting sheath 53 and has an opening on the front end side, this slit 91 being connected to the side holes 57 and enabling insertion of the ligating wire 50 thereinto.

Figure 9:
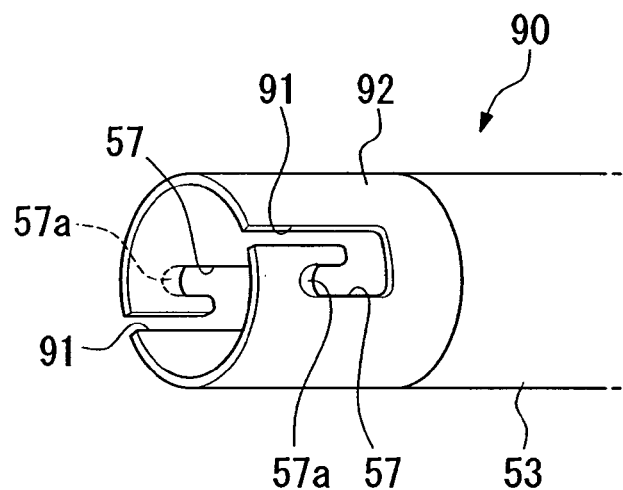
FIG. 9 is a perspective view showing the front end of the cutting sheath in the second embodiment of the medical procedure tool according to the present invention.

In other words, as shown in FIG. 9, the cutting member 92 of this embodiment has a slit 91 which is connected the side holes 57.

Figure 10:
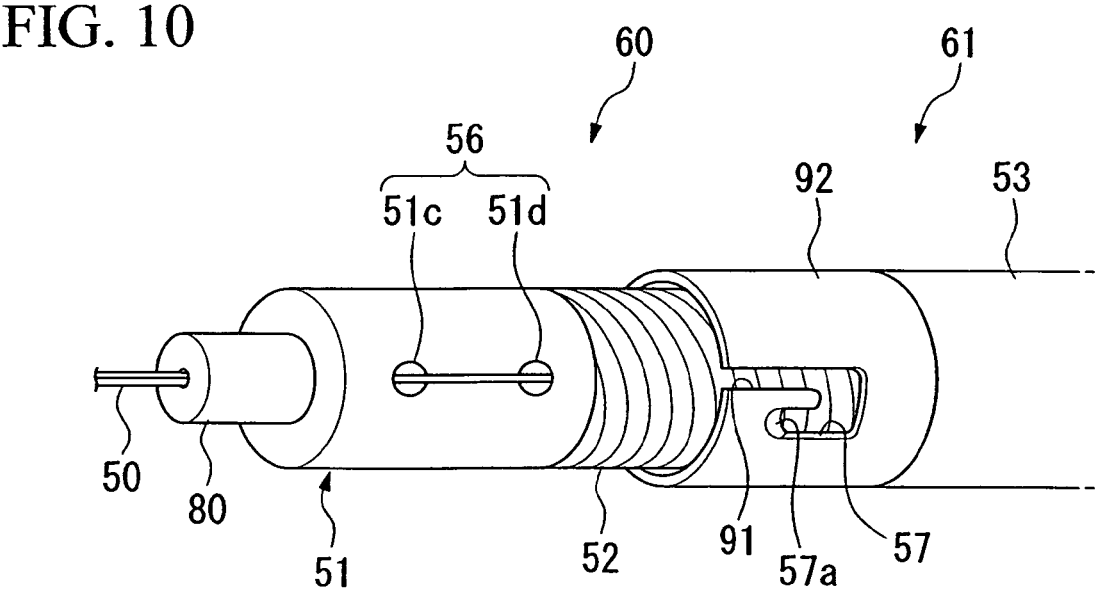
FIG. 10 is a perspective view showing the arrangement prior to attaching the ligating wire, which is exposed on the outside of the wire holding member, inside the side hole of the cutting sheath shown in FIG. 9.

When performing assembly in a medical procedure tool 90 designed in this way, the ligating wire 50 is engaged in the engaging member 66a, after which, the reduced diameter part 51a of the wire holding member 51 is inserted and comes to a halt in the front end of the inner sheath 52, as shown in FIG. 10. In this state, the cutting sheath 53 is moved in the forward direction, and the ligating wire 50, which is exposed outside the wire holding member 51, held in between the front end side holes 51c and the base end side holes 51d, is inserted into the slit 91. After insertion, the cutting sheath 53 is rotated around the axis (i.e., rotated in the direction such that side holes 57 are directed toward the ligating wire 50). As a result, as shown in FIG. 11, the side holes 57 can be positioned at the front end side of the base end side holes 51d. Thus, by retracting the cutting sheath 53 by tugging on the cutting grip 54, cutting can be carried out while holding the ligating wire 50 between the side holes 57 and the base end side holes 51d.

Figure 11:
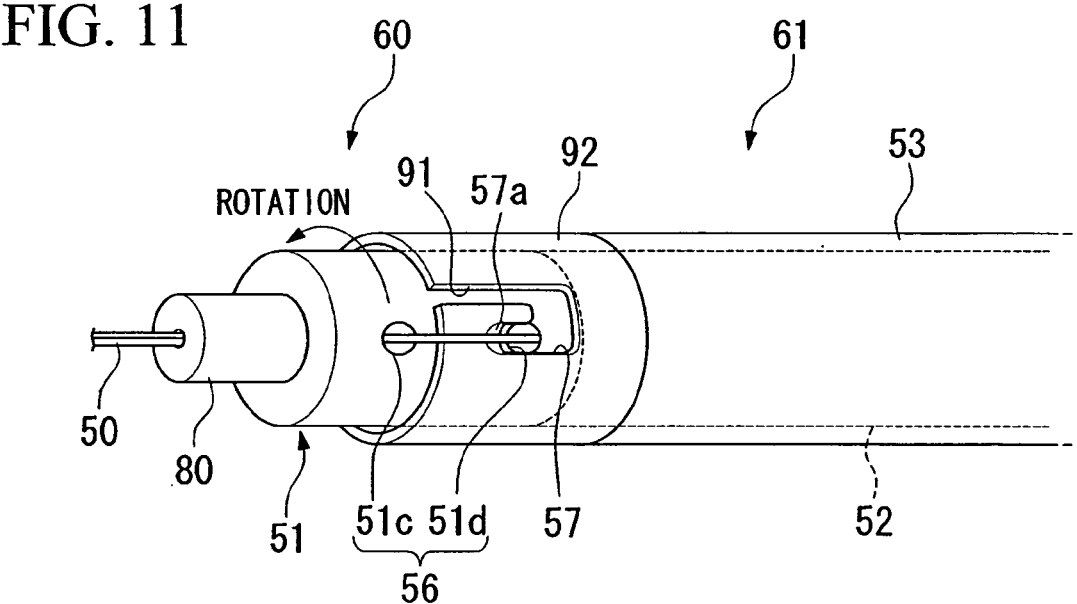
FIG. 11 is a perspective view showing the arrangement in which the ligating wire, which is exposed on the outside of the wire holding member, has been positioned inside the side hole of the cutting sheath, from the state shown in FIG. 10.

Note that when cutting sheath 53 is rotated and disposed to the position for cutting as shown in FIG. 11, it is desirable to temporarily fix the cutting sheath 53 in place inside the inner sheath 52 so that the cutting sheath 53 does not easily move in the axial direction. For example, it is acceptable to form an annular groove to the inner peripheral surface of the cutting sheath 53, and then provide an O-ring to the outer periphery of the inner sheath 52 for engaging in this groove. In this way, the O-ring engages with the groove, making it possible to prevent the cutting sheath 53 from easily moving in the axial direction.

In this medical procedure tool 90 according to the present embodiment, the wire holding member 51 and the cutting sheath 53 are freely attaching and releasing, so that, during assembly, it is not necessary to assemble the wire holding member 51 and the cutting sheath 53 simultaneously. In other words, it is easy for the medical specialist (technician) to easily assemble the medical ligation tool 60 and the operating device 61 prior to use. Accordingly, when carrying out multiple ligations on the same patient, the operating device 61 can be reused, so that it is possible to change only the medical ligation tool 60. As a result, it is possible to reduce the product cost.

Next, a third embodiment of the medical procedure tool according to the present invention will be explained with reference to FIGS. 12 and 13. Note that in the third embodiment, the structural components that are the same as in the first embodiment are assigned the same numeric symbol and an explanation thereof is omitted here.

The point of difference between the first embodiment and the third embodiment is that in the first embodiment, the cutting sheath 53 is a coil sheath, while in the third embodiment, a reinforcing wire 95, which is connected to the side holes 57 and the cutting grip 54, is fixed in place to the cutting sheath 53 of the third embodiment, along the axial direction thereof.

Figure 12:
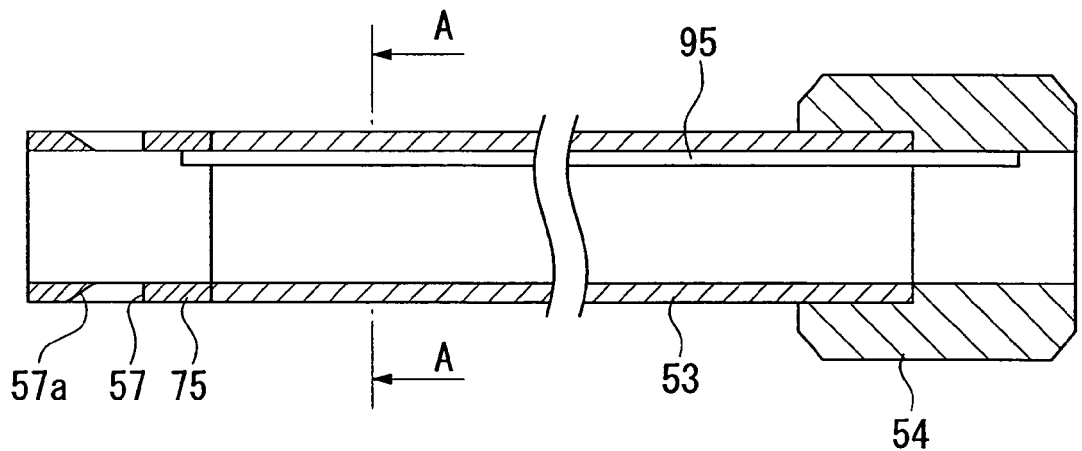
FIG. 12 is a cross-sectional view showing the front end of the cutting sheath in the third embodiment of the medical procedure tool according to the present invention, showing the arrangement in which the reinforcing wire is fixed in place in between the cutting grip and the cutting member.
Figure 13:
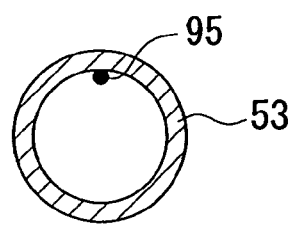
FIG. 13 is a cross-sectional view along the line indicated by arrow A-A shown in FIG. 12.

In other words, in the cutting sheath 53 in this embodiment, as shown in FIGS. 12 and 13, the reinforcing wire 95, which is formed of a metallic member such as stainless, is fixed in place in a unitary manner inside the cutting sheath 53. Note that the reinforcing wire 95 may be either a monofilament or a stranded wire. In addition, the reinforcing wire 95 is fixed in place so that it does not effect the advancing and retracting operation of the inner sheath 52.

As a result of the cutting sheath 53 of this embodiment, it is even more difficult to extend in the axial direction, so that the pulling force at the cutting grip 54 is communicated with greater certainty to the cutting member 75. Accordingly, the ability to cut the ligating wire 50 can be even further improved.

Note that this embodiment employed a single reinforcing wire 95, however, the invention is not limited thereto. Rather, a plurality of reinforcing wires 95 may be used.

Next, a fourth embodiment of the medical procedure tool according to the present invention will now be explained with reference to FIGS. 14 through 17. In this fourth embodiment, compositional elements that are equivalent to those of the first embodiment will be assigned the same numeric symbol and an explanation thereof will be omitted here.

The point of difference between the fourth and first embodiments is that in the first embodiment, the side holes 57 are provided to the cutting member 75 which is connected to the front end of the inner sheath 52, while in the medical procedure tool 100 of the fourth embodiment, the side holes 57 are provided to a cutting member 101 (cutting member) that is freely attaching and releasing with respect to the cutting sheath 52.

Figure 14:
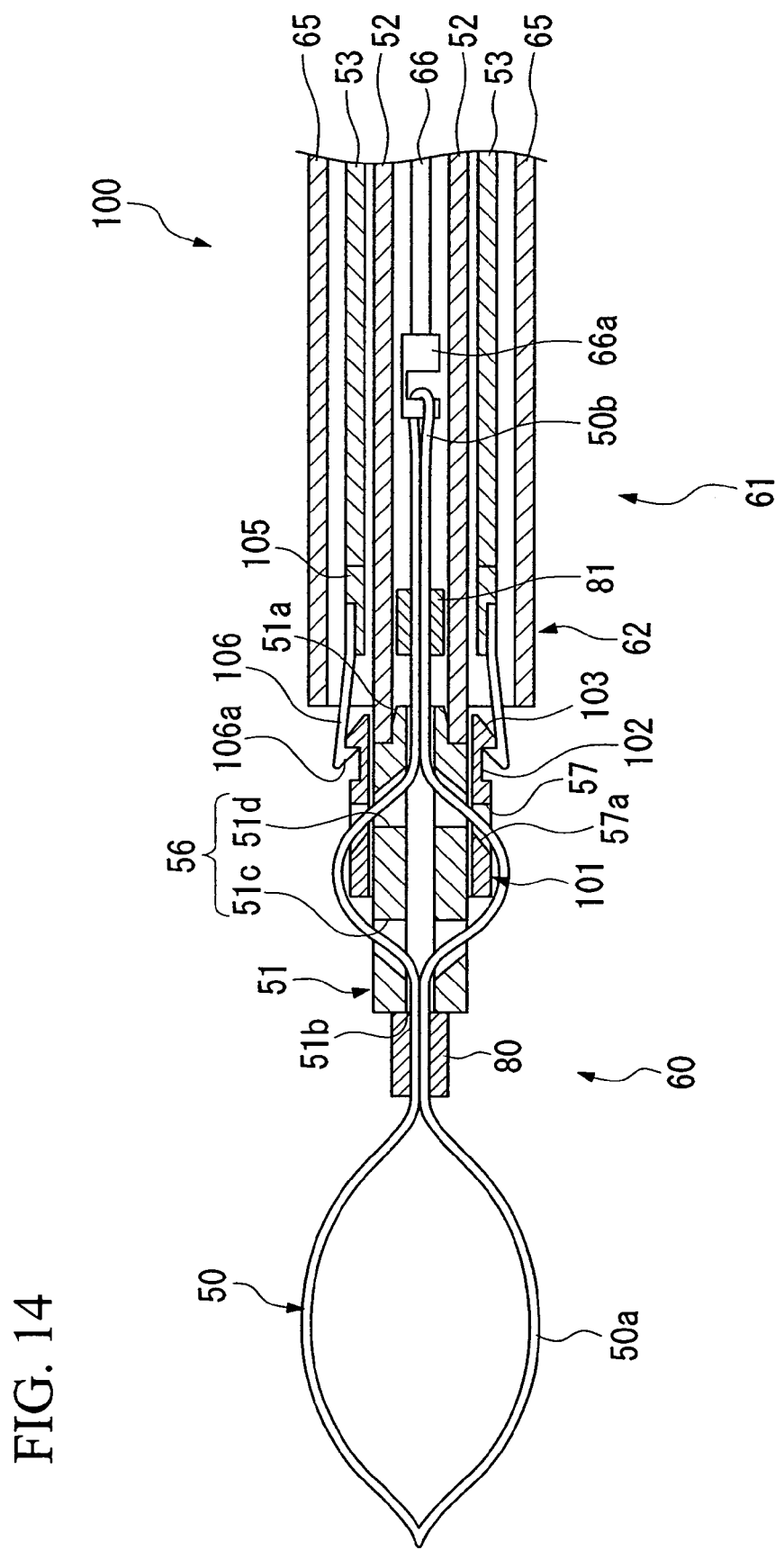
FIG. 14 is a cross-sectional view of the medical ligation tool and the front end of the inserted part showing the fourth embodiment of the medical procedure tool of the present invention.
Figure 15:
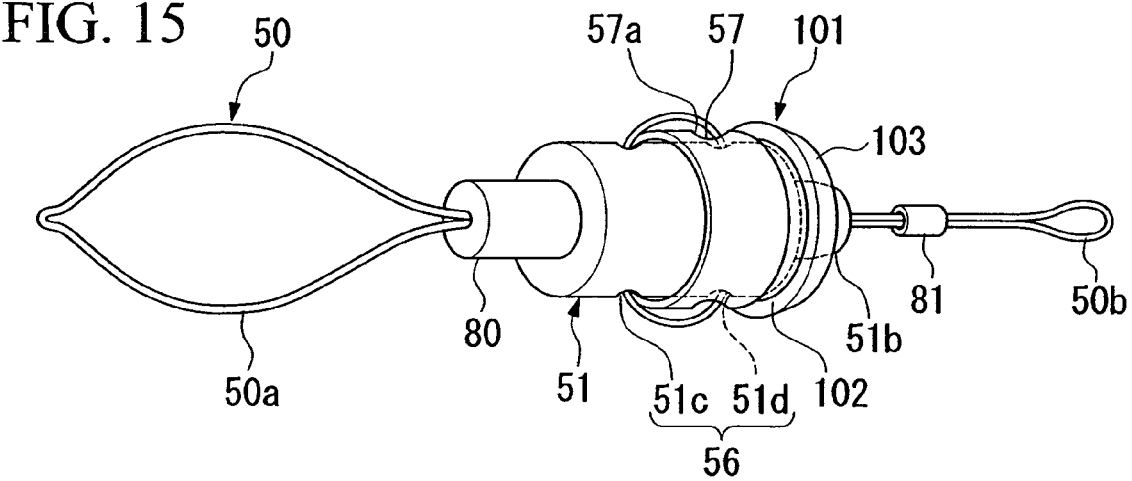
FIG. 15 is a perspective view showing the arrangement in which the cutting member of the medical procedure tool shown in FIG. 14 is attached to the medical ligation tool.

Namely, as shown in FIGS. 14 and 15, the cutting member 101 of this embodiment is composed of a metallic member such as stainless, and is formed in the shape of a cylinder so as to cover the wire holding member 51. Further, a pair of side holes 57 are formed to the front end side of the cutting member 101. An annular groove 102 and a tapered part 103, the diameter of which gradually decreases from the annular groove 102 toward the base end side of the cutting member 101, are formed to the base end side of the side holes 57.

Figure 16:
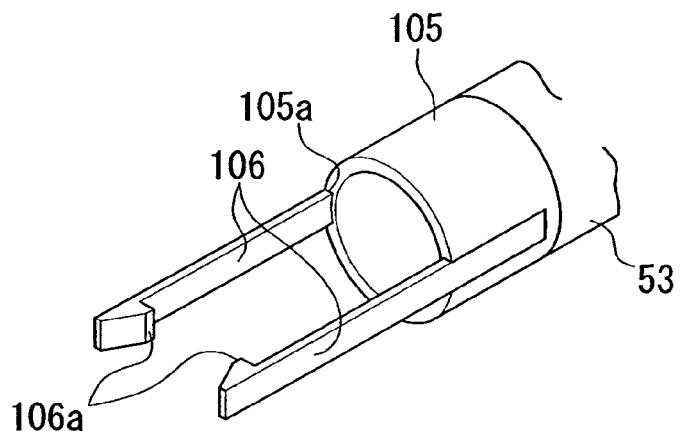
FIG. 16 is a perspective view showing the front end of the cutting sheath of the medical procedure tool shown in FIG. 14.

As shown in FIG. 16, a connecting pipe 105 having outer and inner diameters equivalent to the cutting sheath 53, is connected to the front end of the cutting sheath 53 in this embodiment. A pair of rectangular grooves 105a are formed extending longitudinally from the front end opening in the axial direction on opposite sides to this connecting pipe 105.

A connecting hook 106 which extends in the direction of the front end along the axial direction of the respective cutting sheaths 53 is attached to the groove 105a. In this case, the connecting hook 106 is attached so as to be completely within the groove 105a, so that it does not project out from the outer surface of the connecting pipe 105.

The connecting hook 106 is formed of a metal or plastic material having elasticity, and has a claw 106a which is formed to the front end projecting inward.

As shown in FIG. 15, in the medical procedure tool 100 of this embodiment, the cutting member 101, covered over by the wire holding member 51, is first assembled together with the ligating wire 50. The assembly is performed here so that the side holes 57 are positioned to the front end of the base end side holes 51d of the wire holding member 51. As shown in FIG. 14, by inserting the reduced diameter part 51a of the wire holding member 51 into the front end of the inner sheath 52, the claw part 106a of the connecting hook 106 is caught on the annular groove 102 of the cutting member 101 and stopped. As a result, the cutting sheath 53 and the cutting member 101 enter a state where there are mutually connected. In addition, when the claw part 106a becomes caught in the annular groove 102, the base end side of the annular groove 102 forms a taper part 103, so that the claw part 106a easily engages in the annular groove 102. In other words, a design is provided in which the claw 106a slides over the taper part 103 and easily engages with the annular groove 102 by mean of pushing when the connecting hook 106 is in a state of contact with the taper part 103.

Since the cutting member 101 freely attaches to and releases from the cutting sheath 53 in this way, the cutting member 101 can be exchanged each time cutting is performed. As a result, the cutting ability of the blade member 57a can be maintained without any deterioration in the cutting ability.

Figure 17:
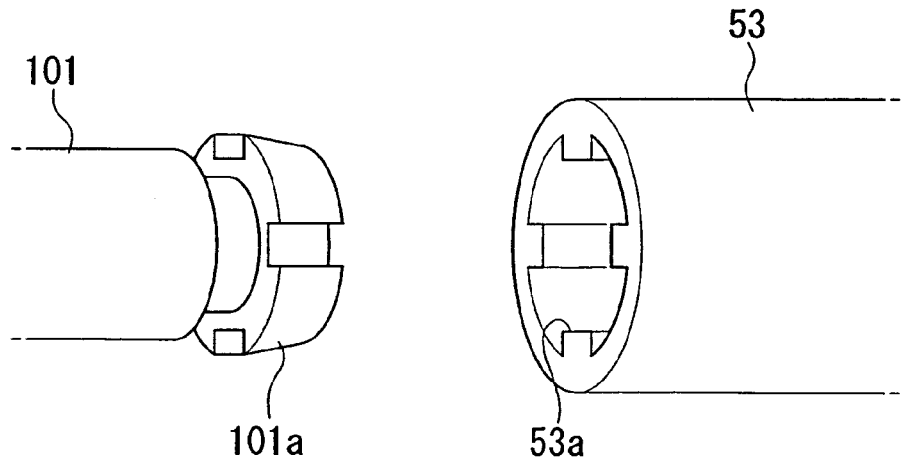
FIG. 17 is a perspective view of the base end side of the cutting member and the front end side of the cutting sheath, showing another example of the medical procedure tool shown in FIG. 14.

In this embodiment, the claw part 106a of the connecting hook 106 is hooked on and stopped in the annular groove 102, rendering cutting member 101 freely attaching and releasing as a result. Note, however, that the present embodiment is not limited to a connecting hook 106; rather, an alternative design is acceptable provided that it is freely attaching and releasing. For example, as shown in FIG. 17, it is also acceptable to design a cutting member 101 that can be freely attached to and released from a cutting sheath 53 by means of two stopping members, namely a first stopping member 101a that is formed to the base end side of the cutting member 101, and a second stopping member 53a that is formed to the inner peripheral surface of the front end side of the cutting sheath 53, this second stopping member 53a having a claw part, not shown in the figures, for fixing in place the first stopping member 101a when the first stopping member 101a is inserted and the cutting sheath 53 is rotated.

The design of the present invention is not limited to the above composition. Namely, it is also acceptable to engage cutting sheath 53 and cutting member 101 by provision of a screw, or other general fixing method that enable free attach and release.

Figure 20:
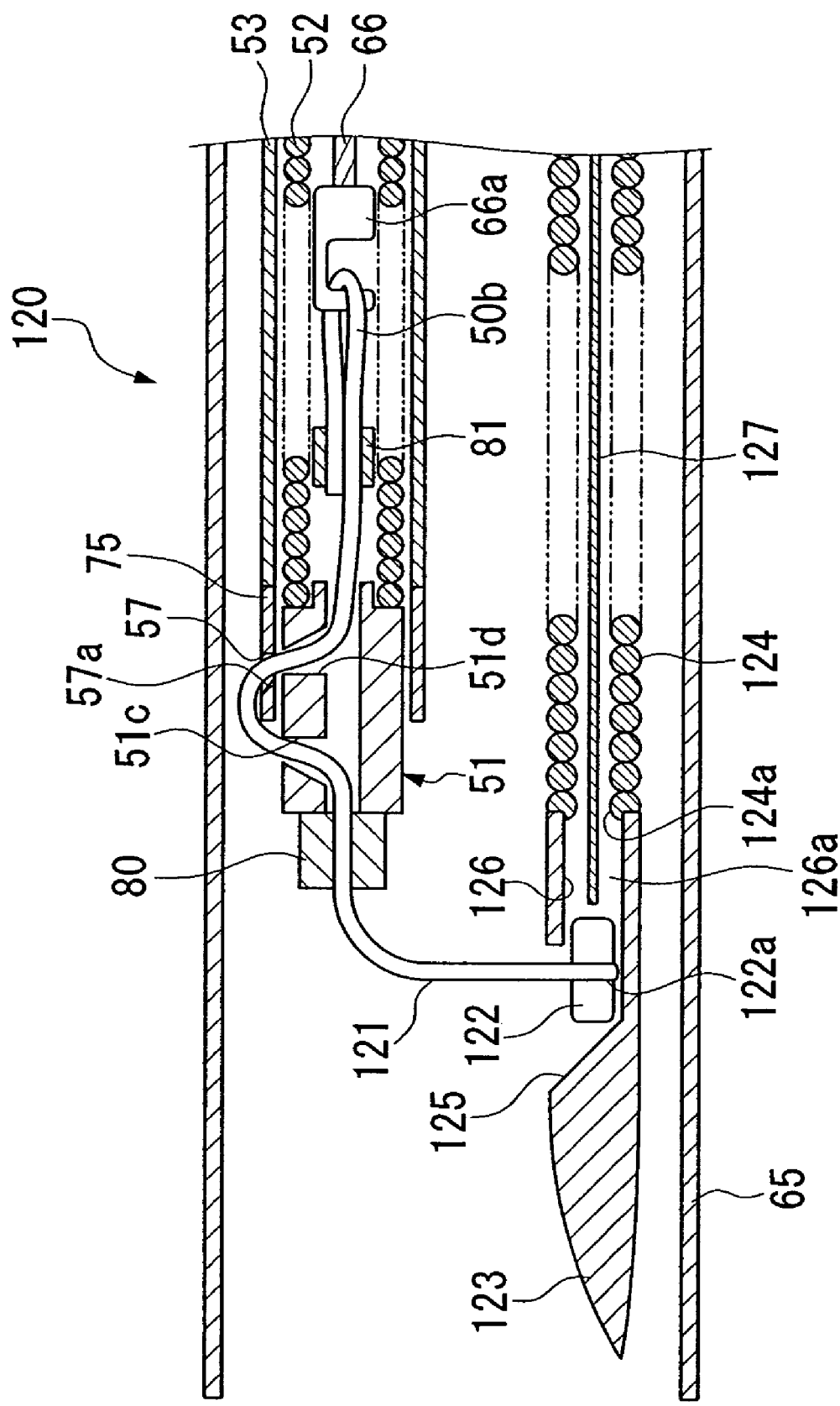
FIG. 20 is a cross-sectional view of the front end of the inserted part, showing a sixth embodiment of the medical procedure tool according to the present invention.

Next, a fifth embodiment of the medical procedure tool according to the present invention will be explained with reference to FIGS. 18 and 20. In this fifth embodiment, compositional elements that are equivalent to those of the fourth embodiment will be assigned the same numeric symbol and an explanation thereof will be omitted here.

The point of difference between the fifth and fourth embodiments is that in the fourth embodiment, the side holes 57 were disposed to a position on the front end side of the base end side holes 51d of the wire holding member 51, while in the medical procedure tool 110 of the fifth embodiment, the side holes 57 are disposed to the front end side of the front end side holes 51c of the wire holding member 51.

Figure 18:
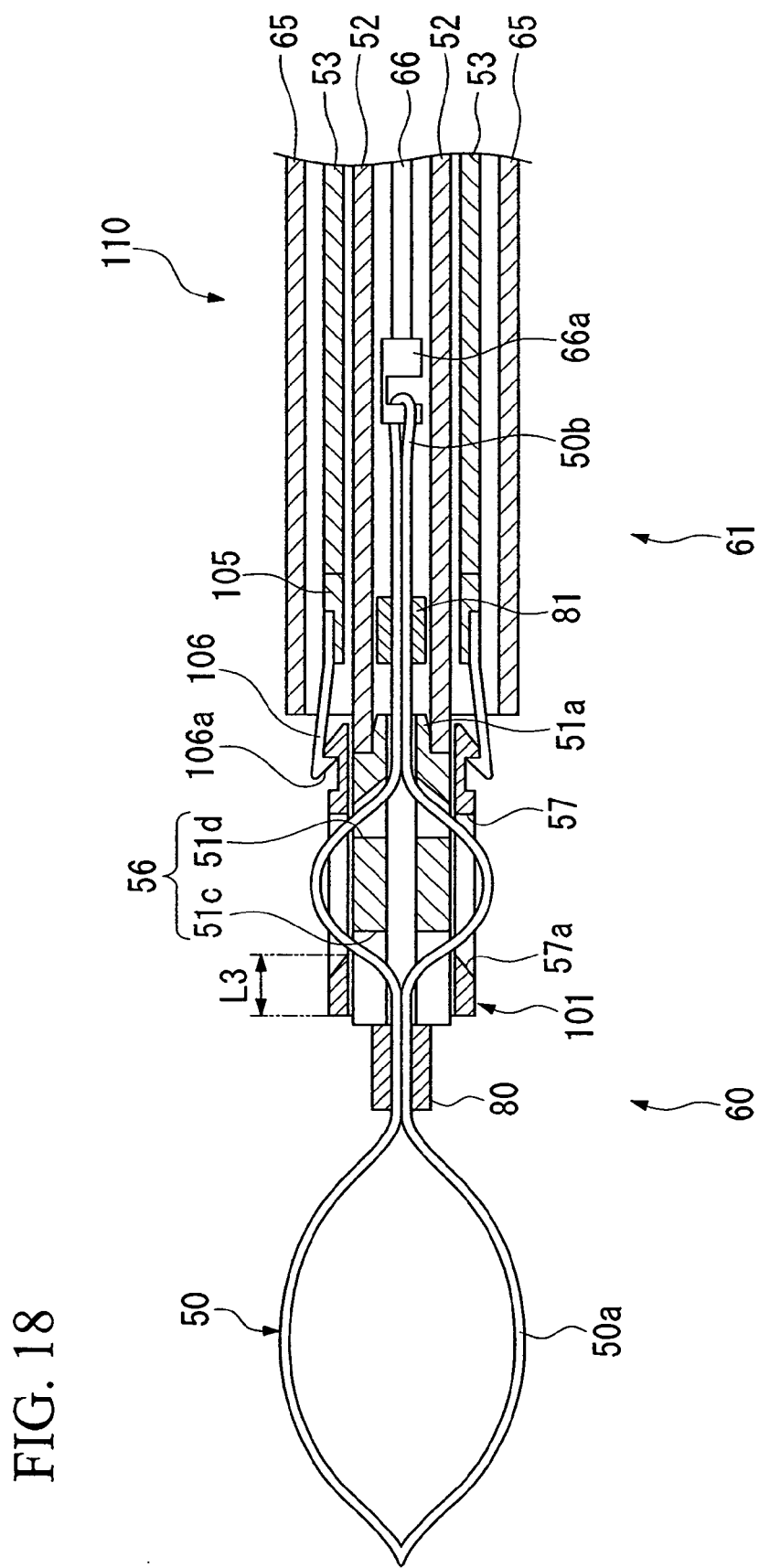
FIG. 18 is a cross-sectional view showing the medical ligation tool and the front end of the inserted part, showing a fifth embodiment of the medical procedure tool according to the present invention.
Figure 19:
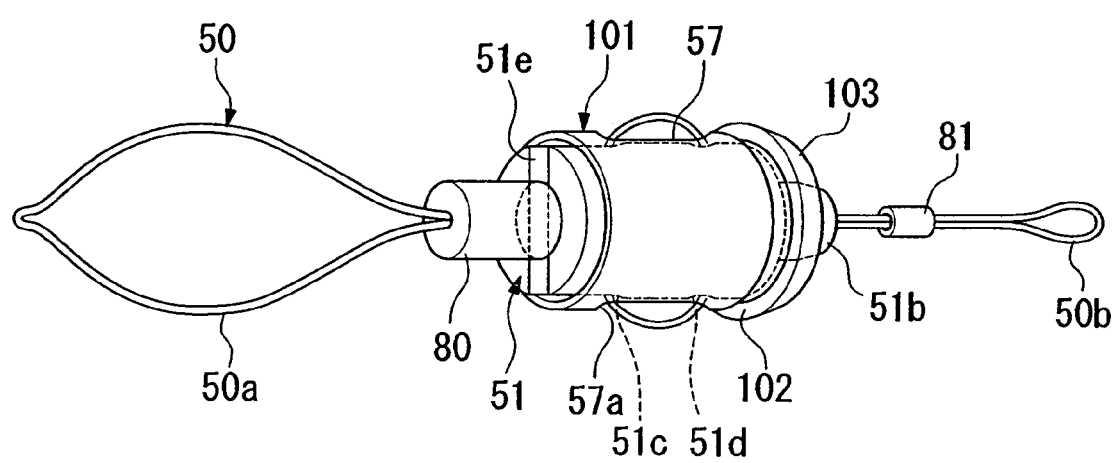
FIG. 19 is a perspective view showing the arrangement in which the cutting member of the medical procedure tool shown in FIG. 18 has been attached to the medical ligation tool.

In other words, in the medical procedure tool 110, the side holes 57 of the cutting member 101 are formed in a slit shape directed along the axial direction as shown in FIGS. 18 and 19. The length thereof is such that the entirely of the ligating wire 50 that is exposed to the outside of the wire holding member 51 in between the front end side holes 51c and the base end side holes 51d can be housed inside. A blade member 57a is formed at a position so that the length L3 from the front end of the cutting member 101 is approximately 1~3 mm. It is preferable that this length L3 be as short as possible.

A front end slit 51e which is connected to the front end side holes 51c is formed to the front end side of the wire holding member 51 in this embodiment.

In a medical procedure tool 110 formed in this way, when the cutting grip 54 is tugged in the base end direction to retract the cutting sheath 53, cutting of the ligating wire 50 is carried out by the cutting member 57a as the ligating wire 50 is held in between the side holes 57 and the front end side holes 51c. Accordingly, after cutting, the length of the ligating wire 50 which remains behind in the body can be made short, and the impact on other procedure tools can be lessened.

When forming the front end side holes 51c of the wire holding member 51, front end slits 51e are formed, rather than forming a pair of holes with good accuracy. As a result, it is possible to simplify the manufacture of the device.

Next, a sixth embodiment of the medical procedure tool according to the present invention will be explained with reference FIGS. 20 through 25. Note that in this sixth embodiment, compositional elements that are equivalent to those of the first embodiment will be assigned the same numeric symbol and an explanation thereof will be omitted here.

The points of difference between the sixth and first embodiments are that in the first embodiment, the medical procedure tool was a ligation device for ligating a lesion site in biological tissue, and that the linear material was ligating wire 50. In contrast, the medical procedure tool 120 in the sixth embodiment is a suturing device for suturing a lesion site which is bleeding, etc., and suture filament 121 is employed as the linear material.

Namely, the medical procedure tool 120 according to this embodiment is equipped with a pull-out preventing tip (pull-out preventing member) 122 which is connected to the front end of the suture filament 121, and a suture needle main body 124, which houses the pull-out preventing tip 122 in a freely attaching and releasing manner and which has a needle part 123 at the tip thereof for penetrating the biological tissue.

The above-described suture needle main body 124 is formed in the shape of a pipe employing a wound coil, and is flexible so as to enable ending inside the instrument channel 4. The needle part 123 is attached to the front end of the suture needle main body 124. The needle part 123 is formed so that the tip thereof has a sharp narrow profile using a metallic member such as stainless, and the outer diameter of the needle part 123 is equivalent to that of suture needle main body 124. A hole 125 is formed to the side surface of the needle part 123. A housing 126 which communicates with the inner hole 124a of the suture needle main body 124 is formed to this hole 125, and is designed to house the pull-out preventing tip 122.

The pull-out preventing tip 122 is cylindrical in shape, with the front end of the suture filament 121 being restrained in an indentation 122a in the center area thereof. The pull-out preventing tip 122 is housed inside housing 126 so that its axial direction coincides with the axial direction of the suture needle main body 124. An engaging hole 126a for engaging with the end of the pull-out preventing tip 122 is formed inside housing 126. The end of the pull-out preventing tip 122 engages in the engaging hole 126a and is thereby housed, so that pull-out preventing tip 122 does not easily fall from the housing 126.

A flexible push-out wire 127 is disposed in a freely advancing and retracting manner inside the inner hole 124a for pushing the pull-out preventing tip 122 housed inside the housing 126 out of the housing 126. This push-out wire 127 can be operated to advance and retract using the hand operator 63.

The suture filament 121 engages with engaging member 66a after passing from pull-out preventing tip 122 through the stopper 80 and the wire holding member 51.

In this embodiment, the outer sheath 65 covers the cutting sheath 53 and the suture needle main body 124. In other words, the suture needle main body 124 is designed to freely advance and retract separately from the cutting sheath 53 inside the outer sheath 65. The suture needle main body 124 can also be manipulated with the hand operator 63.

In addition, the side hole 57, and the front end side hole 51c and base end side hole 51d of the wire holding member 51 are not paired, but rather are formed so that there is one each respectively.

The case where suturing the lesion site using a medical procedure tool 120 designed in this way will now be explained below.

First, the medical specialist determines that the front end of the inserted part 10 of the endoscope has reached the lesion site where the suturing is to be performed using the endoscope image displayed on the monitor 39. Once this determination is made, the medical specialist positions the front end of the endoscope inserted part 10 near the lesion site while observing the monitor 39. Next, in this state, the medical specialist inserts the medical procedure tool 120 into the instrument insertion channel 4 via the instrument insertion port 15. The medical specialist then moves the grip 72 in the forward direction and, as shown in FIG. 20, inserts the outer sheath 65 into the instrument insertion channel 4 with the periphery of the cutting sheath 53 and the suture needle main body 124 covered by the outer sheath 65.

Figure 21:
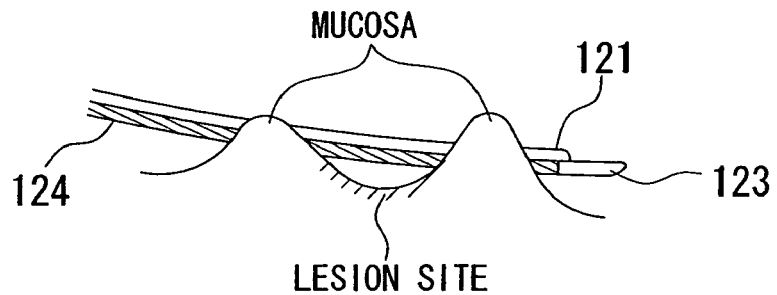
FIG. 21 is a view showing the arrangement in which the mucosa surrounding the lesion site has been penetrated by the suture needle main body of the medical procedure tool shown in FIG. 20.

Using the endoscope image displayed on the monitor 39, the medical specialist then confirms that the outer sheath 65 projects out beyond the front end surface of the endoscope inserted part 10, after which he/she moves the grip 72 in the base end direction, thereby retracting the outer sheath 65. The medical specialist next manipulates the suture needle main body 124 while observing the monitor 39 and, as shown in FIG. 21, penetrates the mucosa on the nearer side around the lesion site where hemostasis is being attempted, and then passed the needle part 123 through the mucosa on the opposite side with the interposed therebetween.

In order not to interfere with the movement of the suture needle main body 124, the suture filament 121 is provided with a sufficiently long length.

Figure 22:
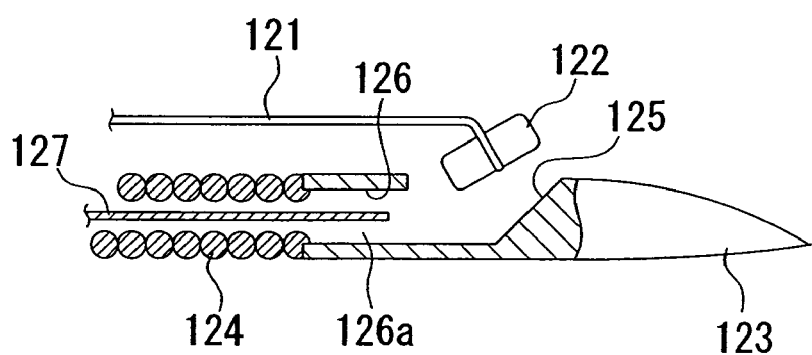
FIG. 22 is a lateral view of the suture needle main body showing the arrangement in which the pull-out preventing tip has been removed from the suture needle main body of the medical procedure tool shown in FIG. 20.
Figure 23:
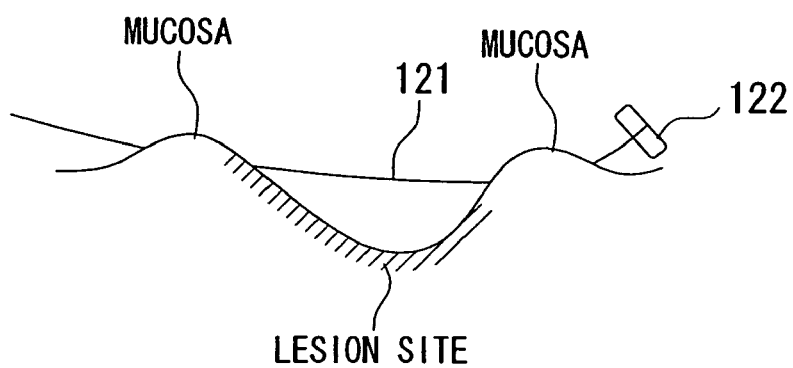
FIG. 23 is a view showing the arrangement in which the suture needle main body has been pulled out from the arrangement shown in FIG. 21.

In this case, as shown in FIG. 22, the push-out wire 127 is pushed out in the forward direction, releasing pull-out preventing tip 122 from the engaging hole 126*a* and pushing it out from the housing 126. As a result, the pull-out preventing tip 122 becomes separated from the suture needle main body 124. By pulling out the suture needle main body 124 after removing the pull-out preventing tip 122, the pull-out preventing tip 122 becomes caught on the biological tissue, as shown in FIG. 23, and the suture filament 121 which is connected to the pull-out preventing tip 122 is passed through both mucosal membrane surface pierced by needle part 123.

Figure 24:
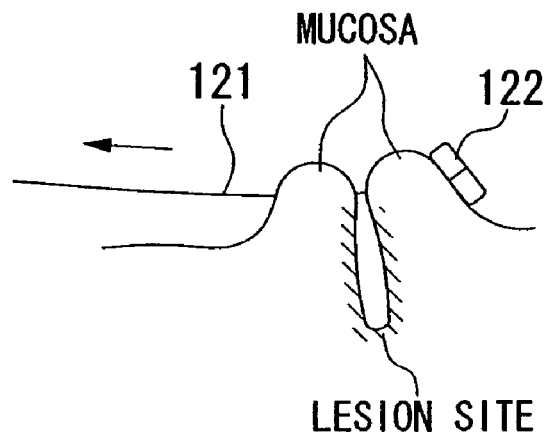
FIG. 24 is a view showing the arrangement in which the suture material has been pulled, causing the mucosa to overlap and close the lesion site.
Figure 25:
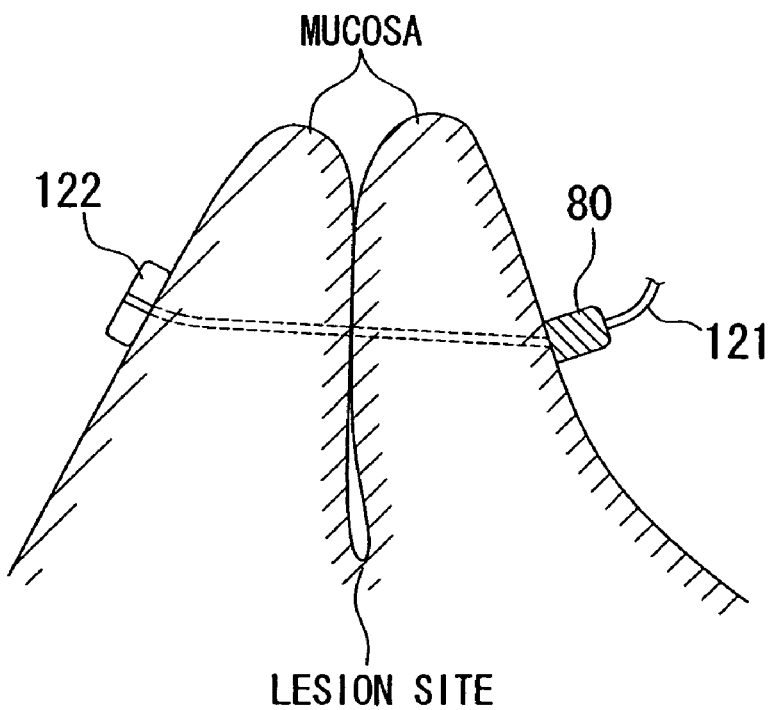
FIG. 25 is a view showing the state where the suture material has been cut and is held in place by a stopper, from the arrangement shown in FIG. 24.

Next, by manipulating the slider 71 in the base end direction by tugging on the operating wire 66*a* in this state, the pierced mucosa is drawn together, as shown in FIG. 24. In other words, the suture filament 121 draws together the pierced mucosa portions, and closes the lesion site which was hemorrhaging. Next, the lesion is sealed in a state such that the stopper 80 is brought into contact with the mucosal membrane portions. Thereafter, the cutting sheath 53 is tugged by moving the cutting grip 54 in the direction of the base end, so that cutting can be carried out with certainty using with blade member 57*a* while holding the suture filament 121 between side holes 57 and base end side holes 51*d*. After cutting the suture filament 121, suturing is performed with the lesion in the closed state, and fixed in place using the stopper 80, as shown in FIG. 25. As a result, the procedure to suture the lesion site is completed.

Note that the technical scope of the present invention is not limited to the above embodiments. Rather, various changes are acceptable within a scope which does not depart from the spirit of the invention.

For example, in the first embodiment, the side holes were disposed to the forward side of the base end side holes of the wire holding member, and the ligating wire was cut between the side hole and the base end side holes. However, the first embodiment is not limited thereto. Rather, it is also acceptable to dispose the side hole farther in the forward direction than the front end holes, and to cut the ligating wire between the side hole and the front end side holes. In this way, the ligating wire after cutting can be made shorter, which is more preferable.

A blade member was provided in each of the preceding embodiments, however, the present invention is not limited thereto. For example, it is also acceptable to provide a first cutting member, i.e., a blade member to the front end side holes or base end side holes of the wire holding member. In other words, a blade member may be provided to either of these, provided that cutting can be carried out while holding the ligating wire between the front end side holes or base end side holes and the side hole.

In the case where employing the medical procedure tool according to this embodiment for the suturing device in the sixth embodiment, is also acceptable to employ the designs disclosed in the second through fifth embodiments as well.

In the medical procedure tool according to the present invention, the lesion site is sutured by operating the suture needle main body while penetrating the biological tissue with the needle part. After suturing, by releasing the pull-out preventing member from the suture needle main body, and pulling on the operator, the suture can be cut with ease and certainty, with the biological tissue remaining in the sutured state. In addition, there is no need for such troublesome procedures as returning the first sheath to its original position after cutting, so that the suturing procedure can be carried out with good efficiency.

In the medical procedure tool according to the present invention, cutting of the linear material can be carried out by a pulling manipulation of the second sheath, so that the first sheath does not fly out and become exposed from the second sheath. Accordingly, there is no need for such troublesome procedures as returning the first sheath into the second sheath following cutting. Further, since cutting is performed while holding the linear material between both cutting parts, cutting of the linear material can be carried out easily and with certainty.

INDUSTRIAL APPLICABILITY

The present invention can be employed as a medical procedure tool that is inserted into a body cavity and is used for carrying out a specific process, such as ligating or suturing, to biological tissue.

As a result of the present invention, a medical procedure tool can be obtained with which it is possible to cut a linear material, such as ligating wire, after performing a specific process on a biological tissue, while at the same time eliminating the requirement to perform troublesome additional procedures after cutting.

The invention claimed is:

1. A medical procedure tool comprising:
    a flexible linear material for carrying out a specific procedure to a biological tissue;
    a linear material holding member provided covering said linear material in a freely advancing and retracting manner, for holding said linear material;
    a flexible first sheath provided so as to come into contact with a base end side of said linear material holding member;
    a flexible second sheath provided covering said first sheath and so as to be freely advancing and retracting with respect to said first sheath and said linear material holding member, and having an inner diameter larger than an outer diameter of at least a portion of the linear material holding member;
    an operator that is connected to a base end side of said second sheath and is for advancing and retracting manipulation of the second sheath; and
    a cutter for cutting said linear material; wherein
    said cutter is provided with a first cutting part provided to said linear material holding member; and a second cutting part that is provided to the front end of said second sheath and which, together with said first cutting part, grips said linear material therebetween;

the second cutting part is a blade member;

said first cutting part has a front end guide for guiding said linear material from inside said linear material holding member to the outside, and a base end guide for guiding said linear material that was guided to the outside by said front end guide back inside;

said second cutting part is disposed farther forward than said base end guide of said first cutting part; and said second cutting part is disposed to a position where said linear material exposed to the outside is held between said second cutting part and said base end guide part in a state in which a base end of said second cutting part holds said linear material, and said cutter is configured and operative to cut said linear material by moving the second sheath in the direction of the base end with respect to said first sheath.

2. A medical procedure tool according to claim 1, wherein said second cutting part is provided to a cutting member that freely attaches to and releases from the second sheath.

3. A medical procedure tool according to claim 1, wherein said first sheath is a coil sheath.

4. A medical procedure tool according to claim 1, wherein said linear material is a ligating wire for ligating biological tissue.

* * * * *